United States Patent
St. Laurent

(10) Patent No.: US 9,492,420 B2
(45) Date of Patent: *Nov. 15, 2016

(54) 3-METHANESULFONYLPROPIONITRILE FOR TREATING INFLAMMATION AND PAIN

(71) Applicant: Olatec Therapeutics LLC, New York, NY (US)

(72) Inventor: Joseph St. Laurent, Lakeville, MA (US)

(73) Assignee: OLATEC THERAPEUTICS LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/639,781

(22) Filed: Mar. 5, 2015

(65) Prior Publication Data

US 2015/0231106 A1    Aug. 20, 2015

Related U.S. Application Data

(60) Continuation of application No. 14/216,664, filed on Mar. 17, 2014, now Pat. No. 8,975,297, which is a continuation of application No. 13/759,676, filed on Feb. 5, 2013, now Pat. No. 8,829,046, which is a division of application No. 13/324,777, filed on Dec. 13, 2011, now Pat. No. 8,476,316.

(60) Provisional application No. 61/423,485, filed on Dec. 15, 2010.

(51) Int. Cl.
*A01N 37/34*    (2006.01)
*A61K 31/275*    (2006.01)

(52) U.S. Cl.
CPC .................................. *A61K 31/275* (2013.01)

(58) Field of Classification Search
None
See application file for complete search history.

(56) References Cited

U.S. PATENT DOCUMENTS

| | | | |
|---|---|---|---|
| 4,424,167 A | 1/1984 | Oeckl | |
| 4,476,137 A | 10/1984 | Haviv et al. | |
| 5,175,192 A | 12/1992 | Ulrich et al. | |
| 5,348,838 A | 9/1994 | Ushirogouchi et al. | |
| 6,551,615 B1 | 4/2003 | Iyer et al. | |
| 2006/0069160 A1 | 3/2006 | Torrence | |
| 2007/0293457 A1 | 12/2007 | Baker et al. | |
| 2009/0291917 A1 | 11/2009 | Akama et al. | |
| 2010/0221336 A1 | 9/2010 | Fink et al. | |
| 2010/0240756 A1 | 9/2010 | St. Laurent | |

FOREIGN PATENT DOCUMENTS

| | | |
|---|---|---|
| EP | 355049 A2 | 2/1990 |
| WO | WO9939713 | 8/1999 |
| WO | WO-9962557 A1 | 12/1999 |
| WO | WO-2007108807 A1 | 9/2007 |
| WO | WO2010018814 | 2/2010 |

OTHER PUBLICATIONS

International Search Report and Written Opinion mailed Aug. 30, 2012 for PCT/US2011/064590.
Armesto, et al.: "First Steps in the Oxidation of Sulfur-Containing Amino Acids by Hypohalogenation: Very Fast Generation of Intermediate Sulfenyl Halides and Halosulfonium Cations". Tetrahedron 56 (2000) p. 1103-1109.
Hsi, et al.: "Synthesis of Some Analogs of Rorifone", Scientia Sinica, vol. 27, No. 6, Dec. 1974.
Juliana, et al.: "Anti-inflammatory Compounds Parthenolide and Bay 11-7082 Are Direct Inhibitors of the Inflammasome". Journal of Biological Chemistry, vol. 285, No. 13. Mar. 26, 2010.
Khlebnikov, et al.: "Compounds with Four and Three Carbon-Heteroatom Bonds". Science of Synthesis, vol. 24 (2005).
Kjaer, et al.: isoThiocyanates VI. A Synthesis of Cheiroline (r-MethylsulphonylpropylisoThiocyanate), Acta Chemica Scandinavica 7 (1953) 1370-1374.
Mayo Clinic; http://www.mayoclinic.com/health/bronchitis/DS00031; Definition of Bronchitis.
Peskin, et al.: Kinetics of the Reactions of Hypochlorous Acid and Amino Acid Chloramines with Thiols, Methionine, and Ascorbate. Free Radical Biology & Medicine, vol. 30, No. 5, p. 572-579, 2001.
Truce, et al.: "Preparation of beta-oxo sulfones by the Thorpe reaction. Acidity of beta-oxo sulfones". Journal of Organic Chemistry. 1962. vol. 27, p. 2821-2828.
Xie, et al.; "Diabetes is an inflammatory disease: evidence from traditional Chinese medicines"; Diabetes Obes. Metab.; vol. 13, No. 4, pp. 289-301 (Apr. 2011).

*Primary Examiner* — Jared Barsky
(74) *Attorney, Agent, or Firm* — Perkins Coie LLP; Viola T. Kung

(57) ABSTRACT

The present invention relates to purified 3-methanesulfonylpropionitrile or a pharmaceutically acceptable salt thereof, and a method for preparing such compound. The compound has at least 90% (w/w) purity. The present invention is also directed to a pharmaceutical composition comprises the purified compound and a pharmaceutically acceptable carrier. The present invention is further directed to a method for treating inflammation, inflammatory-related disorders, or pain, by administering 3-methanesulfonylpropionitrile or a pharmaceutically acceptable salt or solvate thereof to a subject in need thereof.

11 Claims, 2 Drawing Sheets

3-METHANESULFONYLPROPIONITRILE FOR TREATING INFLAMMATION AND PAIN

This application is a continuation of U.S. application Ser. No. 14/216,664, filed Mar. 17, 2014; which is a continuation of U.S. application Ser. No. 13/759,676, filed Feb. 5, 2013, now U.S. Pat. No. 8,829,046; which is a divisional application of U.S. application Ser. No. 13/324,777, filed Dec. 13, 2011, now U.S. Pat. No. 8,476,316; which claims the benefit of U.S. Provisional Application No. 61/423,485, filed Dec. 15, 2010. The contents of the above-identified applications are incorporated herein by reference in their entireties.

FIELD OF THE INVENTION

The present invention relates to a pharmaceutical composition comprising a pharmaceutically acceptable carrier and a compound of 3-methanesulfonylpropionitrile, or its pharmaceutically acceptable salts. The compound is purified to ≥90% purity. The present invention also relates to processes of preparing the compound and methods of using the purified compound for treating inflammation or inflammatory-related disorders and pain.

BACKGROUND OF THE INVENTION

Inflammation is a process by which microbes or tissue injury induce the release of cytokines and chemokines from various cell types producing increased blood vessel permeability, upregulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, namely, mediators, antigens, and autogens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

Current therapies are directed to some or all of the pathogenetic components of inflammation. For example, corticosteroids have a broad spectrum of activities and NSAIDS are more specifically anti-prostaglandin and analgesic. All current therapies have relatively high rates of adverse effects and adverse effects are severe and serious.

There is a need for a composition and a method for treating inflammation, inflammatory-related disorders, and pain. The composition should be economic and easy to manufacture, and the method should be effective and have no significant side effects.

SUMMARY OF THE INVENTION

The present invention is also directed to a pharmaceutical composition comprising a pharmaceutically acceptable carrier and a purified compound of 3-methanesulfonylpropionitrile or a pharmaceutically acceptable salt or solvate thereof. The compound is purified to at least 90% purity (w/w).

The present invention is also directed to a method for treating inflammation, inflammatory-related disorders, and pain. The method comprises the step of administering 3-methanesulfonylpropionitrile or a pharmaceutically acceptable salt thereof to a subject in need thereof. The pharmaceutical composition comprising the active compound can be applied by any accepted mode of administration including topical, oral, and parenteral (such as intravenous, intramuscular, subcutaneous or rectal). Topical administration and oral administration are preferred.

Purified 3-methanesulfonylpropionitrile can be prepared by a method comprising the steps of: (a) mixing methionine, a water-immiscible organic solvent, and a halogenating agent, and reacting at a temperature between 0-35° C.; (b) removing the aqueous phase and obtaining an organic solvent phase; and (c) removing the organic solvent to obtain the compound in an oil form or in a solid form.

Purified 3-methanesulfonylpropionitrile can also be prepared by a method comprising the steps of: (a) mixing methionine, ethyl acetate, and an aqueous hypochlorite solution and reacting at a temperature between 0-35° C., (b) removing the aqueous phase and obtaining an ethyl acetate phase, (c) reducing the ethyl acetate phase volume to 1-20% of its original volume by distillation, vacuum, or nitrogen purging, (d) adding ethanol to the ethyl acetate of (c), (e) removing the ethyl acetate of step (d) and obtaining the compound in the ethanol, (f) reducing the volume of the ethanol of (e) to cause the compound to precipitate and/or crystallize out of the ethanol as a solid, and (g) isolating the solid. This method is suitable for large scale and results in high purity (at least 99%) of the compound.

DETAILED DESCRIPTION OF THE INVENTION

Definition

Figure 1:
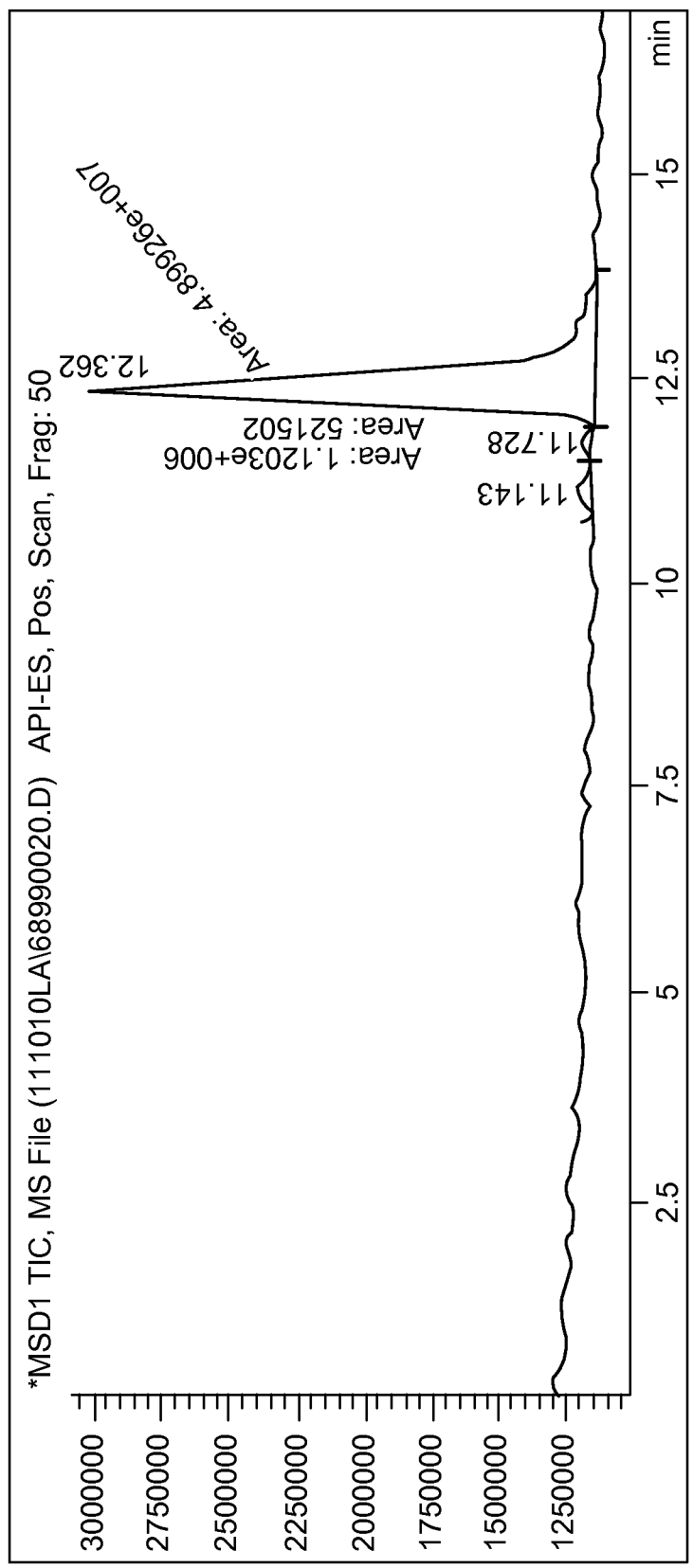
FIG. 1 shows the total ion spectra (HPLC-TIC) of the product of Example 1.

An "adduct", as used herein, is a product of a direct addition of two or more distinct molecules, resulting in a single reaction product containing all atoms of all components. An "adduct ion" is formed from a precursor ion and contains all of the constituent atoms of that ion as well as additional atoms or molecules. Adduct ions are often formed in a mass spectrometer ion source.

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$ (wherein X is $C_{1-4}$).

"Solvates," as used herein, are addition complexes in which the compound is combined with an acceptable co-solvent in some fixed proportion. Co-solvents include, but are not limited to, ethyl acetate, lauryl lactate, myristyl lactate, cetyl lactate, isopropyl myristate, methanol, ethanol, 1-propanol, isopropanol, 1-butanol, isobutanol, tert-butanol, acetone, methyl ethyl ketone, acetonitrile, benzene, toulene, xylene(s), ethylene glycol, dichloromethane, 1,2-dichloroethane, N-methylformamide, N,N-dimethylformamide, N-methylacetamide, pyridine, dioxane, and diethyl ether.

Purified Compound

The present invention is directed to a purified compound of 3-methanesulfonylpropionitrile:

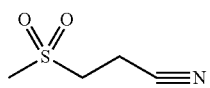

The present invention is also directed to the pharmaceutically acceptable salts, or solvates of 3-methane sulfonylpropionitrile.

The compound preferably has a purity of at least 85%, 90%, 95%, 97%, 98%, or 99%.

The inventor has discovered that 3-methanesulfonylpropionitrile can be prepared by a method comprising the steps of: (a) mixing methionine, a water-immiscible organic solvent, and a halogenating agent, and reacting at a temperature between 0-35° C.; (b) removing the aqueous phase and obtaining an organic solvent phase; and (c) removing the organic solvent to obtain the compound in an oil form or in a solid form.

Methionine can be L-methionine, D-methionine, or a mixture thereof.

Halogenating agents useful for this invention include fluorinating agents, chlorinating agents, and brominating agents. Examples of halogenating agents are hypochlorite, chloramine T, chlorine gas, hydrogen bromide, phosphorus tribromide, phosphorus pentabromide, and 1-chloromethyl-4-fluoro-1,4-diazoniabicyclo[2.2.2]octane bis-(tetrafluoroborate). A preferred chlorinating agent is hypochlorite (e.g., sodium hypochlorite). Commercial bleach CLOROX® contains about 6% hypochlorite, and can be used as a halogenating agent.

The water-immiscible organic solvent useful in this invention is preferably a semi-polar or non-polar solvent having a polarity of about 0.1-7.5, such as ethyl acetate, hexane, heptane, methylene chloride, n-butanol, lauryl lactate, myristyl lactate, cetyl lactate, or isopropyl myristate. A preferred water-immiscible organic solvent is ethyl acetate.

The reaction of step (a) is carried out at a temperature between 0° C. to ambient temperature, for example 0-35° C., preferably 4-30° C., and more preferably 22-28° C. The reaction is preferably carried out under basic conditions, for example, between pH 7.1-14, preferably, pH 7.2-9, or pH 7.5-8.

In one embodiment, methionine is in a solid form and is mixed with a water-immiscible organic solvent and an aqueous halogenating agent. The mixing is optionally carried out under an inert gas, e.g. argon.

In a preferred embodiment, solid methionine is mixed with a water-immiscible organic solvent first and an aqueous halogenating agent is then added to the rapidly stirred suspension. The organic solvent is in excess of water by at least about 2-fold, 5-fold, or 10-fold in volume. "About" as used in this application, refers to ±15% of the recited value. For example, the volume of the organic solvent is about 2-20 fold, 3-10 fold, or 4-6 fold of the water volume. The reaction of methionine and hypochlorite is very fast in water and is difficult to control. The excess organic solvent slows down the reaction, and thus the reaction is more controlled and reproducible. The reaction time is at least 1 hour, 2 hours, 4 hours, 8 hours, or 12 hours, depending on the scale of the production. The reaction time is typically 2-24, or 4-16, or 8-16 hours. The reaction is often carried overnight for convenience.

In a less preferred embodiment, an aqueous solution of a halogenating agent is added to methionine (either in a solid form or an aqueous solution form) and thoroughly mixed, and then the organic solvent is added immediately, After the methionine/halogenating agent reaction occurs, the reactive product partitions in the organic solvent.

The mixing of step (a) can be done by any means of mechanical mixing, for example, impeller stirrer, sheer mixing, rotary mixing, etc.

After the reaction of step (a) is complete, the water-organic solvent mixture is allowed to settle. The organic phase is separated from the water phase by any means known to a skilled person such as decanting or pipetting, and the organic solvent extract containing the reactive product is obtained. Preferably, the organic phase is collected in the presence of sodium sulfate to remove residual water. Any non-soluble residues in the organic solvent extract and sodium sulfate are optionally removed by filtration, decanting, centrifugation, or any means known to a skilled person. The reactive product is stable (without significant oxidation or hydrolysis) in the organic solvent at room temperature (22-28° C.) for at least a month, preferably, 3 months, more preferably 6 months or a year.

In a typical reaction, 10-200 g of methionine, and 200 mL-4 L of 3-12% (e.g. 6%) hypochlorite are used. In a typical extraction, about 1-20 L or more water-immiscible organic solvent is used. The amounts of the above reagents can be scaled up or scaled down proportionally.

In a preferred embodiment, the water-immiscible organic solvent is ethyl acetate. After the aqueous phase is removed, the ethyl acetate solvent is removed from the product by any means known to a person skilled in the art. For example, the ethyl acetate solvent can be removed by evaporation such as rotary evaporation or drying under nitrogen gas. After the ethyl acetate solvent is removed, the product 3-methanesulfonylpropionitrile is obtained in an oil form or in a solid form, which is stored in an enclosed vessel (such as a capped vial or bottle) and is stable for at least 1-3 months at room temperature (22-28° C.).

After the ethyl acetate solvent is removed, the solid product is identified as 3-methanesulfonylpropionitrile by infusion mass spectroscopy, HPLC-MS, Time of Flight High resolution MS, elemental analysis, $^1$H NMR, $^{13}$C NMR, and FTIR.

After the ethyl acetate solvent is removed, the oil or solid product 3-methanesulfonylpropionitrile in general has at least 80% (w/w) purity. The product can be further purified to remove impurities by preparative chromatography such as thin-layer chromatography, column chromatography, and HPLC, recrystalization, solvent washing, or other suitable means. Preferred purification methods include thin-layer chromatography and flash chromatography. After purification, 3-methanesulfonylpropionitrile has purity of at least about 85%, or 90%, or 93%, or 95%, or 98%, or 99%. The synthetic yield of the purification procedure is in general 15-40%.

In another embodiment of the invention, 3-methanesulfonylpropionitrile can be prepared by a process comprising the steps of (a) mixing methionine, ethyl acetate, and an aqueous hypochlorite solution and reacting at a temperature between 0-35° C., (b) removing the aqueous phase and obtaining an ethyl acetate phase, (c) reducing the ethyl acetate phase volume to 1-20% (e.g. 5-10%) of its original volume by distillation, vacuum, or nitrogen purging, (d) adding ethanol to the ethyl acetate of (c), (e) removing the ethyl acetate of step (d) and obtaining the compound in the ethanol, (f) reducing the volume of the ethanol of (e) to cause the compound to precipitate and/or crystallize out of the ethanol solution as a solid, and (g) isolating the solid. The solid is either amorphous powder or in a crystalline form.

In the above process, after step (c) and before step (d), the ethyl acetate solution is optionally dried by a suitable means to remove any residual water, e.g., drying over magnesium sulfate. In the step (d), the volume of ethanol added is the same or in excess of the volume of ethyl acetate. For example, the volume of ethanol can be 1-10 fold (preferably 1-5 fold or 1-3 fold) of that of the ethyl acetate. Ethanol is added to the ethyl acetate phase and azeotropic displacement of ethyl acetate is conducted under vacuum or nitrogen purge. The volume of ethanol is reduced by vacuum, nitrogen purge, or distillation (step (e)). After the solid is precipitate and/or crystallize out of the ethanol solution as a solid, it can be isolated by vacuum filtration. The isolated solid can be dried by suitable means such as ambient air drying or vacuum drying. The solid can be further purified by re-crystallization, re-slurry/precipitation, and/or column purification, to obtain purity of greater than 98 or 99%.

Pharmaceutical Compositions

The present invention provides pharmaceutical compositions comprising one or more pharmaceutically acceptable carriers and 3-methanesulfonylpropionitrile, or a pharmaceutically acceptable salt, or solvate thereof. The active compound 3-methanesulfonylpropionitrile, or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in the dosage forms such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of 3-methanesulfonylpropionitrile may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of 3-methanesulfonylpropionitrile may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethylether.

Topical formulations including 3-methanesulfonylpropionitrile can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, lauryl lactate (for example, at about 0.1-10%, or about 0.2-5%, or about 0.5-5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the compound. Preferably lauryl lactate is purified to achieve ≥90%, preferably ≥95% purity; the high purity mitigates the presence of hydrolytic and oxidative agents. In addition, DMSO at 0.1-20%, or 0.5-10% (w/w) in the formulation provides suitable solubility of 3-methanesulfonylpropionitrile.

In another embodiment, diethylene glycol monoethylether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid resides in many cell membranes. When arachidonic acids are cleaved from the membranes, it can produce many of the known eicosinoids including prostaglandins and leucotrienes, which are known pro-inflammatory entities.

Applicant has discovered that 3-methanesulfonylpropionitrile inhibited pro-inflammatory cytokine release (e.g., IL-1β, IL-6, TNFα, IL-4 and IFNγ) from human peripheral blood mononuclear cells in vitro. Applicant has discovered that 3-methanesulfonylpropionitrile is anti-inflammatory when applied topically in the mouse ear swelling model, in which the inflammation was induced by arachidonic acid. Applicant has found that a gel formulation containing 3-methanesulfonylpropionitrile was well tolerated in 14-day dermal toxicity studies in rats and minipigs. The only effects seen after oral, systemic toxicity administration in rats and dogs were mild physiological effects including decreased body temperature, decreased respiratory rate, increased blood pressure and increased heart rate. The effects were seen at doses over 2000-fold above expected human therapeutic doses, which indicates that the compound would be well tolerated for systemic therapeutic use.

The present invention is directed to a method of treating inflammation and/or pain. The active compound 3-methanesulfonylpropionitrile can be used as is, or it can be administered in the form of a pharmaceutical composition that additionally contains a pharmaceutically acceptable carrier. The method comprise the steps of first identifying a subject suffering from inflammation and/or pain, and administering to the subject 3-methanesulfonylpropionitrile, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestations of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes traumatic pain, neuropathic pain, organ pain, and pain associated with diseases. Traumatic pain includes pain resulting from injury, post-surgical pain and inflammatory pain. Neuropathic pain includes neuropathic and idiopathic pain syndromes, and pain associated with neuropathy such as diabetic neuropathy, causalgia, brachial plexus avulsion, occipital neuralgia, fibromyalgia, gout, and other forms of neuralgia. Organ pain includes ocular, corneal, bone, heart, skin/burn, visceral (kidney, gall bladder, etc.), joint, and muscle pain. Pain associated with diseases includes pain associated with cancer, AIDS, arthritis, herpes and migraine. The present invention reduces pain of varying severity, i.e. mild, moderate and severe pain; acute and chronic pain. The present invention is effective in treating joint pain, muscle pain, tendon pain, and burn pain.

In preferred embodiments, the present invention is useful in treating inflammation and/or pain associated in a musculoskeletal system or on the skin. The highly innervated, musculoskeletal and skin systems have a high capacity for demonstration of pain. In addition, the musculoskeletal system has a high capacity for tissue swelling, and the skin has a high capacity for redness, swelling, and heat. In musculoskeletal and skin systems, the degree of tissue damage is frequently magnified out of proportion to the resulting inflammatory response. In the skin for example, merely firm stroking will cause release of the cytokines, IL-1 and TNF.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. The skeletal or muscular diseases or conditions include musculoskeletal sprains, musculoskeletal strains, tendonopathy, peripheral radiculopathy, rheumatoid arthritis, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epichondylitis (pitchers elbow) and trochanteric bursitis, temporomandibular joint syndrome, and fibromyalgia.

The present invention provides a method for treating inflammation and/or pain associated with inflammatory skin diseases such as dermatitis and psoriasis. The method comprises the steps of identifying a subject in need thereof, and administering to the subject the active compound, in an amount effective to treat inflammation and/or pain.

Skin is highly reactive to environmental stimuli and the epidermal component of keratinocytes is a very rich source of both arachidonic acid and pro-inflammatory cytokines of IL-1 and TNF. The skin dendritic cells, Langerhans cells, recognize and process antigens for further immune response of various lymphocytes and all of these cells are primarily regulated by cytokines through their specific cell surface receptors.

Dermatitis (also called eczema) is generic inflammation of the skin. Specific types of dermatitis include atopic, contact, nummular, and photo-induced.

Contact dermatitis has two types, the non-specific irritant type and the antigen specific allergic type. Both involve innate and acquired immune system response including arachidonic acid and cytokine components that initiate and propagate the disease through cell to cell messaging by eicosanoid and/or cytokine moieties produced by epidermal cells, macrophages, dendritic cells, neutrophils, eosinophils, and various T and B lymphocytes.

Atopic dermatitis is eventually a specifically Th2 lymphocyte mediated disease. The initiator of atopic dermatitis is stimuli of epidermal keratinocytes, arachidonic acid and cytokine release. It is established that eicosanoid inhibitors such as prostaglandin inhibitors and cytokine inhibitors such as cyclosporine, tacrolimus, and various specific cytokine receptor monoclonal antibodies reduce the symptoms of atopic dermatitis.

Psoriasis is currently believed to be initiated by some type of injury or microbial stimulus to the epidermis, which causes arachidonic acid and cytokine release and initiates and propagates an inappropriate immune response, which causes the disease. Inhibition of these changes by various eicosanoid and cytokine inhibitors such as prostaglandin inhibitors and cyclosporine and the newer monoclonal antibodies directed against specific cell surface receptors for cytokines has been demonstrated to improve the disease.

3-methanesulfonylpropionitrile, which is effective in inhibiting arachidonic acid induced inflammation and in inhibiting the release of pro-inflammatory cytokine, is effective to treat inflammation and/or pain associated with psoriasis and dermatitis, particularly contact dermatitis, and atopic dermatitis.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of active compounds delivered can vary; but are generally $1\times10^{-10}$-$1\times10^{-4}$ moles/liter, and preferably $1\times10^{-8}$-$1\times10^{-5}$ moles/liter.

In one embodiment, the composition is applied topically onto the affected area and rubbed into it. The composition is topically applied at least one or two times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally 1-50, and preferably 1-5 mg/kg/day.

In one embodiment, the pharmaceutical composition is administrated subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1

Preparation of Product (Starting Material 15 g)

DL-Methionine (approximately 15 g, 100 mmol) was weighed into a 2 L reaction flask. 1.5 L of reagent grade ethyl acetate was added to the flask and to the rapidly stirred via mechanical means. To the suspension was added 310 mL of CLOROX® bleach (about 6% sodium hypochlorite). The flask was capped and stirring was continued at room temperature for about 18 hours.

The mixture was transferred to a separatory funnel, the lower aqueous phase was drained off. The organic layer was dried over sodium sulfate to remove water, and then filtered and washed with 225 mL of ethyl acetate.

The organic phase was added to a 2 L Erlenmeyer flask and concentrated by nitrogen purge to about 230 mL volume. It was transferred to a to a 0.5 L Erlenmeyer flask with 5 mL rinse of ethyl acetate and was concentrated further by nitrogen purge to an off white powder and submitted for analysis. This material was confirmed to be 3-methanesulfonylpropionitrile sodium adduct with 97% purity (see Example 3).

Example 2

Preparation of Product (Starting Material 109 g)

DL-Methionine (approximately 109 g, 716 mmol) was weighed into a 20 L reactor containing 10.9 L of reagent grade ethyl acetate and to the rapidly stirred suspension was added 2200 mL (2420 g) of CLOROX® bleach (1951 mmol). The reactor was capped and stirring was continued at room temperature for a period of 18 hrs.

Stirring was halted and the mixture was allowed to settle for 30 minutes. The lower aqueous phase was drained off. The organic layer was dried over magnesium sulfate, and filtered and washed with an approximate additional 2 L of ethyl acetate, which resulted in approximately 13 L of organic phase.

Incrementally the organic phase was added to 6 L rotary evaporator at 30 mbar, bath temperature of 22° C. and condenser temperature of −4° C., until it was concentrated to about 5% of the initial volume (approximately 0.65 L). An equal volume of ethanol (Absolute, 200 Proof, ≥99.5%, ACS Reagent) was added and azeotropic displacement of ethyl acetate was conducted by maintaining the pot volume (about 1.3 L) with incremental additions of ethanol, which resulted in the precipitation of a white solid in ethanol. The resulting slurry was filtered, washed with ethanol, and dried; the solid was collected as 18.3 g of 92% pure material (Crop 1). The filtrates were refrigerated overnight, which resulted in additional solid precipitate being formed; the solid precipitate was collected by vacuum filtration, washed with ethanol, and dried to yield 4.2 g (Crop 2) with a purity of 96%.

The first and second crops were combined in a 500 mL round bottom flask with 250 mL ethanol, heated to 55-60° C. and slowly cooled to 5±3° C. After completion of a two hour age, the product slurry was filtered, washed with cold ethanol, and dried by vacuum, which yielded 21.3 g of 99.7% pure material in a solid form.

The purity and identification of the material (3-methanesulfonylpropionitrile sodium adduct) were confirmed by the HPLC-MS method described in Example 3.

Example 3

Identification of Product as 3-Methanesulfonylpropionitrile

The isolated product of Example 1 was analyzed by infusion mass spectroscopy, HPLC-MS, Pos mode, Time of Flight High resolution MS, Elemental analysis, $^1$H and $^{13}$C NMR and FTIR.

1. HPLC-MS

HPLC-MS Instrument Parameters are listed in Table 1 below.

TABLE 1

| Instrument: | Agilent model 1100 w/MSD |
|---|---|
| Mobile Phase: | 85% Methanol, 13% Ethanol, 2% IPA and 0.1% TFA |
| Flow: | 0.3 mL/min |
| Stop Time: | 17 min |
| Column Temp: | 30° C. |
| Injection Volume: | 0.5 μL |
| Source: | Electrospray |
| Polarity: | Positive |
| Gas Temp: | 350° C. |
| Drying Gas Flow: | 13.0 L/min |
| Nebulizer Press: | 60 psig |
| Scan Parameters | Mass Range: 50-500 AMU Fragmentor Voltage: 50 V |

Figure 2:
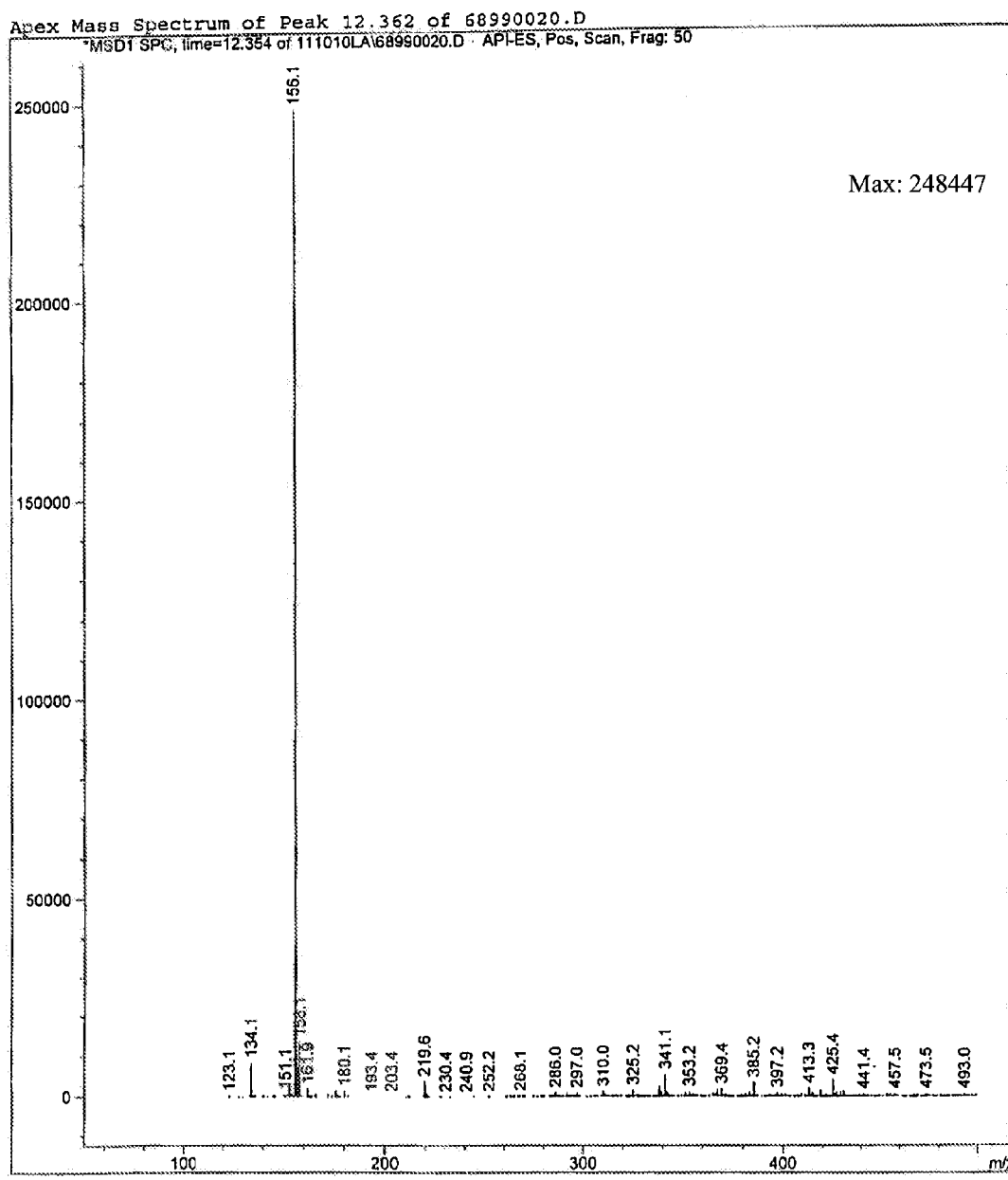
FIG. 2 shows the mass spectra analysis results (HPLC-MS) of the product of Example 1.

Total ion spectra were collected from 75 to 500 AMU (Atomic mass unit). The Total Ion Chromatogram (FIG. 1) demonstrates that the test sample has purity of 96.76% (at 12.3 minute) based on total area under curve. FIG. 2 is the mass spectrum of the 12.3 minute peak from FIG. 1. FIG. 2 depicts the intensity of the signal versus the mass to charge ratio (directly relevant to the molecular weight). FIG. 2 depicts the major isolated ion as 156.1 AMU and a minor ion as 134.1, which is consistent with the product being 3-methanesulfonylpropionitrile with a molecular weight (M) of 133.1, assayed as the M+1 (M+proton, 134.1) and M+23 (M+Na, 156.1, sodium adduct) by mass spectroscopy.

2. TOF High Resolution MS

TOF High Resolution MS Instrument Parameters are listed in Table 2.

TABLE 2

| Instrument: | Waters ACQUITY UHPLC- QTof micro mass spectrometer & LockSpray accurate mass inlet installed |
|---|---|
| Mobile Phase: | 85% Methanol, 13% Ethanol, 2% IPA and 0.1% TFA |
| Flow: | 0.3 mL/min |
| Stop Time: | 20 min |
| Column Temp: | 30° C. |
| Injection Volume: | 1.0 μL |
| Source: | Electrospray |
| Polarity: | Positive |
| Capillary voltage: | 2500 V |
| Sample Cone voltage: | 15.0 V |
| Extraction Cone voltage: | 1.5 V |
| Desolvation Temp: | 300° C. |
| Source Temp: | 110° C. |
| Cone gas flow: | 10 L/hr |
| Desolvation gas flow: | 600 L/hr |

The time of flight (TOF) high resolution HPLC-MS chromatogram peak at 12.3 minutes contains an ion at 156.0078 m/z in its spectrum. The ion observed at 156.0078 m/z in the spectrum of the chromatographic peak at 12.3 minutes is likely a sodium adduct. The elemental composition of the sodium adduct is $C_4H_7NO_2S$+Na with an error of 10.9 ppm. The high resolution TOF data supports the HPLC ES-MS data that the test sample of Example 1 is 3-methanesulfonylpropionitrile with a molecular weight 133 AMU.

3. Elemental Analysis

The elemental analysis data resulted in elemental composition of 36.385% C, 5.560% H, 10.304% N, 25.14% S provides supporting data of the elemental composition of the compound as $C_4H_7NO_2S$.

4. 1H NMR

1H NMR Instrument Parameters are listed in Table 3.

TABLE 3

| Solvent | $CD_3OD$ |
|---|---|
| Transmitter Nucleus | Proton |
| Spectrometer Frequency (sfrq) (MHz) | 399.798 |
| Temp (° C.) | 25 |
| D1 (sec) | 5 |
| Spin (Hz) | 20 |
| Processing (1D) LB (Hz) | 0.2 |
| # points acquired | 35k |
| Pw (us) | 6 |
| Processing size (fn) | 64k |
| Sweep width (sw) (kHz) | 7 |
| Number of Transients (nt) | 40 |

The 1H NMR spectrum was acquired in $CD_3OD$ solution at 400 MHz by Spectral Data Services, Inc. The 1H NMR spectrum comprises three discrete and integratable signals, as shown in Table 4.

TABLE 4

| $^1$H Chemical shifts (ppm) and coupling constants (J in Hz) in $CD_3OD$. | | | | | |
|---|---|---|---|---|---|
| Chemical Shift (ppm) | RIV[a] | Number of Protons | Multiplicity | J (Hz) | Assignment |
| 2.989 | 20.00 | 2 | t | 7.05 | C$\underline{H}_2$ |
| 3.056 | 28.79 | 3 | s | | C$\underline{H}_3$ |
| 3.488 | 19.37 | 2 | t | 7.05 | C$\underline{H}_2$ |

[a]Relative Integration Value

There is also the characteristic $CD_3OD$ multiplet centered at 3.307 ppm and minor impurity peaks at: ~1.1 ppm (RIV=0.11); ~2.1 ppm (RIV=0.16); ~4.2 ppm (RIV=0.08); ~4.6 ppm (RIV=0.02); 4.79 ppm (RIV=0.08).

The 1H NMR spectrum is indicative of a general structure shown below that includes: (a) adjacent methylene groups, each of which is attached to a unique electron withdrawing group/heteroatom (b) an isolated methyl group, which is attached to an electron withdrawing group/heteroatom:

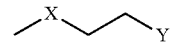

X and Y are electron withdrawing groups/heteroatoms

5. $C^{13}$ NMR $C^{13}$ NMR Parameters are listed below in Table 5.

TABLE 5

| Solvent | $CD_3OD$ |
|---|---|
| Transmitter Nucleus | Carbon |

TABLE 5-continued

| Spectrometer Frequency (sfrq) (MHz) | 100.590 |
| Temp (° C.) | 25 |
| D1 (sec) | 5 |
| Spin (Hz) | 0 |
| Processing (1D) LB (Hz) | 3 |
| # points acquired | 17664 |
| Pw (us) | 15 |
| Processing size (fn) | 32k |
| Sweep width (sw) (kHz) | 25.2 |
| Number of Transients (nt) | 500 |
| Decoupler Nuclei (dn) | H |
| Decoupler Frequency | 399.797 |
| Dmm | www |
| Dm | yyy |

The 13C NMR spectrum was acquired in $CD_3OD$ solution at 100 MHz by Spectral Data Services, Inc. The 13C NMR spectrum comprises four discrete, integratable signals, as shown in Table 6.

TABLE 6

$^{13}C$ Chemical shift data.

| Chemical shift (ppm) | Arbitrary Assignment |
|---|---|
| 118.641 | CN |
| 50.285 | C(alkyl)X |
| 41.029 | C(alkyl)Y |
| 12.068 | C(alkyl)Z |

The 13C NMR spectrum indicates four unique types of carbon atoms. The data is corroborative of the 1H NMR data, only if X or Y in structure 1 is carbon. The line at 118 ppm is characteristic of a nitrile group, i.e., Y=CN. The remaining two signals are suggestive of carbons attached to a heteroatom other than oxygen and, since the compound resulted from chemistry where methionine was the starting material, it is reasonable that atom X is sulfur, giving rise to the following structure:

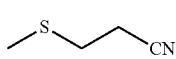

Structure A

Considering the chemistry employed (treatment of methionine with excess sodium hypochlorite in the form of aqueous bleach), S-oxidation would be unavoidable, giving rise to structures the following structures:

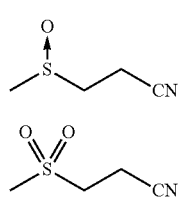

Structure B

Structure C

The mass spectrum acquired displayed a prominent ion at m/z 156, and a lesser ion at m/z 134. The latter ion is consistent with the parent ion of structure C acquired in the positive mode, i.e., M+1, whereas the former ion is likely a sodium ion adduct (M+23). Further support for structure C has been provided by high-resolution mass spectroscopy, which gave an exact mass of 156.0078, which is consistent with a molecular formula of C4H7NaNO2S. Therefore, the proton and carbon 13 NMR spectra are supportive of the structure of 3-methanesulfonylpropionitrile.

6. Fourier Transform Infrared Spectrometer (FTIR)

Fourier Transform Infrared Spectrometer (FTIR) Instrument Parameters are listed below in Table 7.

TABLE 7

| Spectral reflectance Probe | Yes |
| Scan range (cm−1) | 650-4000 |
| Mode | % T |
| Mode range (%) | 26.8-100 |

The FTIR data depicts a spectra consistent with the presence of the nitrile functionality with a N≡C stretch at 2255.7 cm-1 and strong bands at 1129.5 and 1276.5 consistent with the presence of

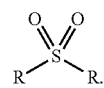

The resultant spectrum is supportive of the structure of 3-methanesulfonylpropionitrile.

Example 4

Gel Formulation 1

Table 8 exemplifies one gel formulation containing 3-methanesulfonylpropionitrile.

TABLE 8

| | 5% Gel | 1% Gel |
|---|---|---|
| 3-methanesulfonylpropionitrile | 5.0% | 1.0% |
| Dow Corning Elastomer Blend EL-8050 ID | 61.0% | 69.0% |
| Labrafac Lipophile WL 1349 | 8.0% | 8.0% |
| Octisalate | 5.0% | 5.0% |
| Lauryl Lactate | 1.1% | 3.2% |
| Dimethyl Sulfoxide (DMSO) | 8.9% | 1.8% |
| Dow Corning 556 Cosmetic Grade Fluid | 7.0% | 7.9% |
| Squalene | 2.0% | 2.0% |
| Sunflower Seed Oil | 2.0% | 2.0% |
| Dow Corning Aerogel VM-2270 | 0.1% | 0.0% |
| | 100.0% | 100.0% |

Example 5

Gel Formulation 2

Table 9 exemplifies another gel formulation containing 3-methanesulfonylpropionitrile.

TABLE 9

| | 5% Gel |
|---|---|
| 3-methanesulfonylpropionitrile | 5.0% |
| Diethylene Glycol Monoethylether | 5.0% |
| Acrylates/C10-30 alkyl acrylate crosspolymer (CARBOPOL ® Ultrez 20 polymer) | 0.50% |
| Trolamine (tris(2-hydroxyethyl)amine) | 0.47% |
| Purified Water | 89.03% |
| | 100.0% |

Example 6

Anti-Inflammatory and Analgesic Activity of 3-methanesulfonylpropionitrile (Prophetic Example)

Purified 3-methanesulfonylpropionitrile (MSPN, prepared according to Example 2) is prepared in the gel formulation according to Example 5. Test materials: MSPN in gel formulation (1-5%), indomethacin (positive control), and vehicle (gel formulation without active compound) are evaluated for anti-inflammatory and analgesic activity in the rat carrageenan-induced paw inflammation model.

Rats are used in the experiment. Carrageenan (0.1 mL of a 1% suspension) is injected subcutaneously into the left hind paw to induce inflammation. MSPN (1-5%) or vehicle gel is applied to the paw topically at volumes of 0.05, 0.1 0.15 or 2.0 mL, 1.5, 2.5, and 3.5 hours following the carrageenan administration. Indomethacin is given orally at 5 mg/kg, 1 hour prior to carrageenan administration. The degree of inflammation (edema, or swelling) is determined using a plethysmograph to measure paw volume. Analgesia is determined by measuring paw withdrawal to a mechanical stimulus using von Frey filaments. Inflammation and analgesia are measured 4 hours after carrageenan administration. MSPN is expected to have anti-inflammatory and/or analgesic properties as measured by a significant decrease in paw volume and/or a significant increase in mechanical pressure needed to elicit paw withdrawal, respectively, as compared to the vehicle control (t-test, $p<0.05$).

Example 7

Analgesic Activity of 3-methanesulfonylpropionitrile (Prophetic Example)

Purified 3-methanesulfonylpropionitrile (MSPN, prepared according to Example 2) is prepared in the gel formulation according to Example 5. Test materials: active compound in gel formulation (1-5%), morphine (positive control), and vehicle (gel formulation without active compound) are evaluated for analgesic activity in the rat hot plate model.

Rats are used in the experiment. MSPN (1-5%) or vehicle gel is applied to the paw topically at volumes of 0.05, 0.1 0.15 or 2.0 mL. One hour later the rat is placed on a 55° C. hot plate, and the time to lick the paw is measured. The positive control, morphine, is given orally at 30 mg/kg, 1 hour prior to hot plate testing. MSPN are expected to have analgesic properties as measured by a significant increase in time to licking as compared to the vehicle control (t-test, $p<0.05$).

Example 8

Treatment of Knee Pain (Prophetic Example)

Objectives:
To investigate the efficacy of 3-methanesulfonylpropionitrile in a gel formulation in patients with mild to moderate knee pain associated with osteoarthritis following temporary cessation of standard NSAID therapy.

Formulation:
The gel formulation contains 3-methanesulfonylpropionitrile at 1% and 5% (Example 5) are used in this example. Placebo contains the same gel without the active compound.

Methodology:
A randomized, double-blind, placebo controlled, parallel treatment multicenter Phase 2 clinical activity study.

Patients with painful osteoarthritis of the knee, controlled by a stable dose of standard NSAID therapy for at least 2 months, discontinue use of the NSAIDs for a 7 day washout period. Patients are then randomized in a 1:1:1 ratio (1% active gel, 5% active gel, placebo). A total of up to 150 patients are enrolled and treated for 7 days with follow-up at 8, 10, 14 and 21 days.

The active Gel or placebo is applied to the affected knee 3 times a day for 7 days for a total of 21 treatments given every 4-6 hours while awake.

Patients are treated for 7 days and followed up for a further 14 days. NSAIDs may be restarted after the Day 10 visit.

Criteria for Evaluation:
Safety:
Adverse Events (AEs) throughout the study.
Physical examination at enrollment (−7 days, start of NSAID washout period), Baseline (Day 1, start of treatment), Day 10 and Day 21.
Vital signs at enrollment (−7 days, start of NSAID washout period), Baseline (Day 1, start of treatment) and Days 2, 4, 8, 10, 14 and 21.
Clinical laboratory measurements at Baseline (Day 1), Day 8 and Day 14.

Clinical Activity:
The primary clinical activity parameters are the measurement of pain at the site of application, as quantified by VAS and the Western Ontario and McMaster University (WOMAC) scale. The effect of treatment on swelling, tenderness and inflammation of the knee is recorded, also the time to reduction or eradication of pain after treatment is recorded.

Study Endpoints:
The primary clinical activity endpoint is:
Change from Baseline (Day 1) to Day 8 in WOMAC functional disability index:
Pain (Scale 0-20).
Stiffness (Scale 0-8).
Physical function (Scale 0-68).
The secondary clinical activity endpoints are:
Change from Baseline (Day 1) to Day 8 in VAS pain scale (1-100).
Within-day change in VAS pain scale on Day 2 and Day 3 as measured by change from daily Baseline (Pre-Treatment 1) to 30 minutes Post Treatment 2.
Change in investigator evaluation of swelling, tenderness and inflammation between Baseline (Day 1) and 30 minutes and 60 minutes after the first application on Day 1.
Change in investigator evaluation of swelling, tenderness and inflammation between Baseline (Day 1) and Day 8.
Time to reduction or eradication of pain subsequent to each topical application of active gel or placebo gel.
Use of rescue medication (APAP).

Example 9

Inhibition of Cytokine Activities 3-methanesulfonylpropionitrile (MSPN, prepared according to Example 1 was tested for its effects on in vitro cytokine release from human peripheral blood mononuclear cells (PBMCs). Secretion of cytokines by PBMCs plays a significant role in the inflammatory response.

MSPN was added to cultures of fresh human PBMCs at 162 μM (22 μg/mL) in duplicate. One hour later, PBMCs were stimulated to secrete cytokines using the mitogens lipopolysaccharide and concanavalin A (ConA). Lipopolysaccharide at 50 pg/mL was used to stimulate the release of interleukin IL-1β, IL-6 and tumor necrosis factor TNFα. ConA at 20 μg/mL was used to stimulate the release of IL-4 and ConA at 5 μg/mL was used to stimulate interferon IFNγ. The corticosteroid dexamethasone (100 nM) was used as a positive control. After 24 hours of incubation, the supernatants were assayed for the cytokines using the Luminex Bead kit. MSPN at 22 μg/mL inhibited the release of IL-1β, IL-6, TNFα, IL-4 and IFNγ by 95%, 98%, 98%, 7% and 21%, respectively. Dexamethasone inhibited the release of IL-1β, IL-6, TNFα, IL-4 and IFNγ by 24%, 60%, 42%, 93% and 87%, respectively.

The results demonstrate that MSPN has a significant inhibitory effect on cytokines involved in the inflammatory process.

Example 10

Anti-Inflammatory Activity of 3-methanesulfonylpropionitrile in Mice

Purified 3-methanesulfonylpropionitrile (MSPN, prepared according to Example 2) was dissolved in vehicle (ethanol/acetone 1:1) to 5% (w/v). The active compound, indomethacin (positive control in vehicle), and vehicle were evaluated for anti-inflammatory activity in the topical arachidonic acid induced ear swelling model in mice.

Male ICR derived mice weighing 22±2 g were used in this experiment. 5 mice were used for each group (active compound, positive control, and vehicle). All animals were maintained in a controlled temperature (22-24° C.) and humidity (60%-70%) environment with 12-hour light/dark cycles for at least one week prior to use.

Arachidonic acid (2 mg in 20 μL acetone) was applied topically onto the anterior and posterior surfaces of the right ear of test animals to induce inflammation. MSPN in vehicle (20 μL), indomethacin (0.3 mg) in vehicle, and vehicle (20 μL) was each applied 30 minutes before and 15 minutes after arachidonic acid challenge. At 90 minutes after arachidonic acid induction of ear edema, the thickness of the right ear and the left ear was measured and the difference calculated as an indication of the inflammation in the right ear. Significant activity is defined as a reduction (inhibition) in arachidonic acid induced ear swelling by ≥30% relative to the vehicle-treated group.

MSPN and indomethacin both caused a significant decrease (31 and 60%, respectively) in the ear swelling induced by arachidonic acid at 90 minutes, relative to the vehicle-treated group (acetone:ethanol/1:1). The difference between MSPN-treated mice and vehicle-treated mice was also determined to be statistically significant (p-value determined by t-test was <0.05).

Example 11

Systemic Administration of MSPN Formulation

This study was done to determine the systemic (plasma) exposure of MSPN after administration by the oral and subcutaneous routes to rats.

MSPN substance was prepared in water for oral administration and in saline for subcutaneous administration. Rats weighed 282 to 295 g were used in the study. Male rats (n=2) were given a single dose at 50, 160 or 500 mg/kg by both oral and subcutaneous routes. Female rats (n=2) were dosed only at 500 mg/kg by both oral and subcutaneous routes. The blood was drawn from each rat at 0.25, 1, 2, 3, 4, 6, 12, 24, and 48 hours and measured for MSPN concentration by LC/MS/MS.

For males, the average maximum plasma concentrations measured (Cmax) after oral dosing at 50, 160 or 500 mg/kg were 160, 560 and 12,000 μg/mL, respectively; and after subcutaneous dosing were 160, 760 and 3300 μg/mL, respectively. For females, the average Cmax after oral dosing of 500 mg/kg was 3800 μg/mL, and after subcutaneous dosing of 500 mg/kg was 9500 μg/mL. Half-lives were similar by both routes and for both sexes, and ranged from 8 to 15 hours.

The above results demonstrate that there was significant bioavailability of MSPN after both the oral and subcutaneous routes.

Example 12

Treating Pain and/or Inflammation Emanating from Ligaments, Tendons, Muscles, Joints, Bones, and Fascia in Humans Materials Each patient was provided with a gel formulation containing 5% of 3-methanesulfonylpropionitrile (see Example 5).

Treatment of Knee

Patient A is 73-year old male whose right knee has a long history of compromise and 3 surgeries. Following 2 days of skiing, patient's right knee was swollen and sore. There was particular discomfort in the tendon that runs along the outside right of the knee. There was also pronounced tenderness underneath the bottom portion of the kneecap. Circumference of the knee was 16⅞ inches.

Patient A applied the 5% gel formulation on the right knees twice 7 hours apart. Three hours after the second application, there was no noticeable swelling on the knee and no pain under kneecap. There was only slight discomfort remaining on outside ligament. The circumference of knee after treatment was 16⅜ inches, which is a reduction of ½ inches.

Treatment of Finger

Patient A also has a long history of arthritis in fingers of the left hand, especially in the middle finger. Patient A felt noticeable swelling, discomfort, and troubling stiffness in the middle finger and was unable to bend the finger beyond 45°. Circumference of knuckle of the middle finger was 3 5/16 inches.

Patient A applied the 5% gel formulation on the middle finger once. About 9 hours after treatment, patient noticed that the stiffness of the finger was relieved and there was no remaining discomfort. Patient A was able to fully bend the middle finger to make a closed fist. Circumference of knuckle of the middle finger after treatment was 2 15/16 inches, which is a reduction of ⅜ inches.

Treatment of Neck

Patient B is a female at age 74, who 15 years ago had both a nerve stimulator implanted, and had a nerve decompression surgery in her neck. For 15 years, Patient B was pain free. In 2011, the same pain from 15 years ago returned. Patient B applied one treatment of 5% gel formulation. After rubbing it in well, she then applied a heating pad for about one hour on the neck. Patient B recorded that pain and discomfort was relieved for several hours, prior to the next application. Patient B repeated this treatment 3 times per day for 2 days and each time recorded that her pain was relieved.

Patient C is an 88-year old male. Patient C pulled muscles in the back of his lower neck after swinging a 6-pound indoor training golf club. Three hours later the pain was excruciating. Patient C applied the 5% gel formulation; at that time Patient C recorded that the pain was a 10 on a scale of 1 to 10 (10 being the worst). The pain remained intense during the next fours hours; Patient C recorded that during this time the pain only dropped to an 8 on the scale. Then the second application of the 5% gel formulation was made and by the end of the next 6 hours, Patient C said the pain had dropped down to a 4 on the scale. Then the third application of 5% gel formulation was made. Four hours later, Patient C recorded that the pain dropped down to a 1 on the scale and stayed there for next six hours, at which time the fourth and final application was made. Within the next six hours, all pain was eliminated.

Patient D is a 59-year old male. After approximately a 30-mile bike ride, Patient D aggravated an arthritic condition in his neck and aggravated strained muscles in the back of his lower neck. After rubbing in only one application the 5% gel formulation, Patient D felt major relief of pain and stiffness within one hour.

Treatment of Shoulder

Patient E is a 58-year old male. Patient E developed and experienced left shoulder pain below the rotator cuff and into the bicep for seven days from playing golf. Patient E continued to play golf and his injury was not healing. Patient E applied the 5% gel formulation twice a day for 3 subsequent days while continuing to play golf. Patient E felt immediate reduction of pain after each application of the 5% gel formulation, and all pain and inflammation was eliminated after 3 days.

Treatment of Hand & Fingers

Patient F is a 74-year old male. Patient F pulled tendons in thumb when playing golf. Patient F felt excruciating soreness and saw visible swelling on thumb. Immediately after the golf game, Patient F applied the 5% gel formulation to the afflicted area of his thumb. Within four hours, the pain had dramatically reduced and the range of motion of the thumb had improved. Four hours later before bed, Patient F applied another treatment and the pain and swelling continued to be reduced. By the next morning, pain was entirely eliminated and swelling was eliminated.

Patient G is a 72-year old man who had chronic arthritis flare-ups in his fingers. Patient G had a flare-up of arthritis in his right thumb. There was no noticeable swelling, but there was a strong aching pain that was pervasive to the entire thumb. The pain was so bad that he could not use his right hand. Patient G applied one application of the 5% gel formulation all over his entire right thumb and massaged it in for about 5 minutes. After six hours, all pain was eliminated.

Treatment of Wrist

Patient F also suffers from chronic pain and inflammation on the wrist, also referred to as gout-like symptoms. When Patient F felt pain and inflammation on the wrist, he applied the 5% gel formulation on wrist three times a day every six hours for 2 days. Patient F felt relief one hour after the first application and by the end of the 2 days, pain and discomfort was removed. Patient F has done this treatment several times.

Treatment of Ankle

Patient F further suffers from a chronic condition of achilles tendonitis in his right ankle. When his ankle flared up, it usually took a 'cycle' of 10 days to two weeks to return back to normal. When the patient applied 5% gel formulation on ankle three times a day for 2 days, the recovery 'cycle' time to normal is reduced by half the number of days.

Treatment of Chest

Patient H is a 55-year old female who has had a chronic condition of costochondritis. When Patient H had flare-up, she experienced sharp stabbing-like pains and tenderness in the area of her sternum. The pain debilitated her for days. With the onset of pain, Patient H applied the 5% gel formulation on afflicted area every 6 hours for two to four days. Within 2 hours of first application, pain was substantially reduced. After 24 hours of treatment (3 applications), Patient H debilitating feeling and soreness to touch was eliminated. Dull pain remained through the second day of application. With repeated applications, dull pain was eliminated and Patient H stopped treatment.

Treatment of Fascia

Patient I is an 85-year old female who has a chronic condition of plantar fascitis in her right foot. When she suffered an onset of pain, Patient I applied the 5% gel formulation on the bottom of her foot and massaged it in for about 5 minutes. Patient I typically did this treatment at night before bed, and once during the day when she stayed off her foot for several hours. Three hours after treatment, patient felt initial reduction of pain. Within 24 hours of treatment, pain was eliminated.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method of reducing or alleviating symptoms of localized manifestations of inflammation characterized by acute or chronic swelling, pain, or redness, comprising the steps of:
    identifying a subject suffering from localized manifestations of inflammation, and
    orally administering to the subject a compound of 3-methanesulfonylpropionitrile, or a pharmaceutically acceptable salt thereof, in an amount effective to treat the localized manifestations of inflammation.

2. The method according to claim 1, wherein said symptoms are characterized by localized acute or chronic swelling.

3. The method according to claim 1, wherein said compound is administered in an oral form of capsule, tablet, or syrup.

4. The method according to claim 1, wherein said compound is administered in an oral form of capsule or tablet.

5. A method of treating inflammation and/or pain, both associated with inflammatory joints, ligaments, tendons, bone, muscles, or fascia, comprising the steps of:
    identifying a subject in need thereof, and
    orally administering to the subject 3-methanesulfonylpropionitrile, or a pharmaceutically acceptable salt thereof, in an amount effective to treat the inflammation and/or pain associated with joints, ligaments, tendons, bone, muscles, or fascia.

6. The method according to claim 5, wherein said method treats inflammation and/or pain associated with rheumatoid arthritis.

7. The method according to claim 5, wherein said method treats inflammation and/or pain associated with osteoarthritis.

8. The method according to claim 5, wherein said method treats inflammation and/or pain associated with gout.

9. The method according to claim 5, wherein said method treats inflammation and/or pain associated with tendonitis.

10. The method according to claim 5, wherein said compound is administered in an oral form of capsule, tablet, or syrup.

11. The method according to claim 10, wherein said compound is administered in an oral form of capsule or tablet.

* * * * *